United States Patent [19]
Lorenzo et al.

[11] Patent Number: 5,993,424
[45] Date of Patent: *Nov. 30, 1999

[54] GUIDEWIRE HAVING A DISTAL TIP THAT CAN CHANGE ITS SHAPE WITHIN A VESSEL

[75] Inventors: Juan A. Lorenzo, Davie; Carol Barbre, Miami Lakes, both of Fla.

[73] Assignee: Cordis Corporation, Miami, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/803,962

[22] Filed: Feb. 21, 1997

Related U.S. Application Data

[63] Continuation-in-part of application No. 08/693,378, Aug. 5, 1996, abandoned.

[51] Int. Cl.[6] ................................................ A61M 5/178
[52] U.S. Cl. ......................... 604/164; 604/528; 604/530
[58] Field of Search ............................ 604/164, 95, 96, 604/166, 170, 264, 280–282, 523, 528–532; 600/433–435, 585, 151

[56] References Cited

U.S. PATENT DOCUMENTS

| | | |
|---|---|---|
| 4,643,194 | 2/1987 | Fogarty . |
| 4,676,249 | 6/1987 | Arenas et al. . |
| 4,779,628 | 10/1988 | Machek . |
| 4,873,983 | 10/1989 | Winters . |
| 4,895,168 | 1/1990 | Machek . |
| 5,040,543 | 8/1991 | Badera et al. . |
| 5,067,957 | 11/1991 | Jervis . |
| 5,143,085 | 9/1992 | Wilson ................................. 128/772 |
| 5,211,636 | 5/1993 | Mische . |
| 5,389,073 | 2/1995 | Imran . |
| 5,419,340 | 5/1995 | Stevens . |
| 5,489,270 | 2/1996 | Van Erp . |

FOREIGN PATENT DOCUMENTS

| | | | |
|---|---|---|---|
| 363 661 | 4/1990 | European Pat. Off. | ....... A61M 25/01 |
| 480 427 | 4/1992 | European Pat. Off. | ....... A61M 25/01 |
| 646 364 | 5/1995 | European Pat. Off. | .......... A61F 2/02 |
| 739 641 | 10/1996 | European Pat. Off. | ....... A61M 25/01 |
| 778 043 | 11/1997 | European Pat. Off. | ....... A61M 25/09 |
| 823 261 | 11/1998 | European Pat. Off. | ....... A61M 25/09 |

*Primary Examiner*—Corrine McDermott
*Assistant Examiner*—Michael J. Hayes
*Attorney, Agent, or Firm*—Dean Garner

[57] ABSTRACT

In accordance with the present invention there is provided a guidewire for navigating through body vessels. The guidewire has a proximal end, a distal end and a longitudinal axis extending therebetween. The guidewire includes an outer tube having proximal and distal ends, wherein the distal end of the tube is a flexible distal tip having a smooth closed distal end. The guidewire further includes a core wire having distal and proximal ends. The core wire distal end is elastic and will return to a preformed shape upon the removal of any stress applied thereto. The core wire can slide longitudinally within the tube between a retracted position, where the core wire distal end is proximal to the flexible distal tip. In the retracted position the tube applies sufficient stress to deform the core wire distal end. The core wire also slides to an extended position, wherein said core wire distal end is within and substantially surrounded by the flexible distal tip. Placing the core wire in the extended position removes the stress so that said core wire distal end and the flexible distal tip assume the preformed shape.

21 Claims, 4 Drawing Sheets

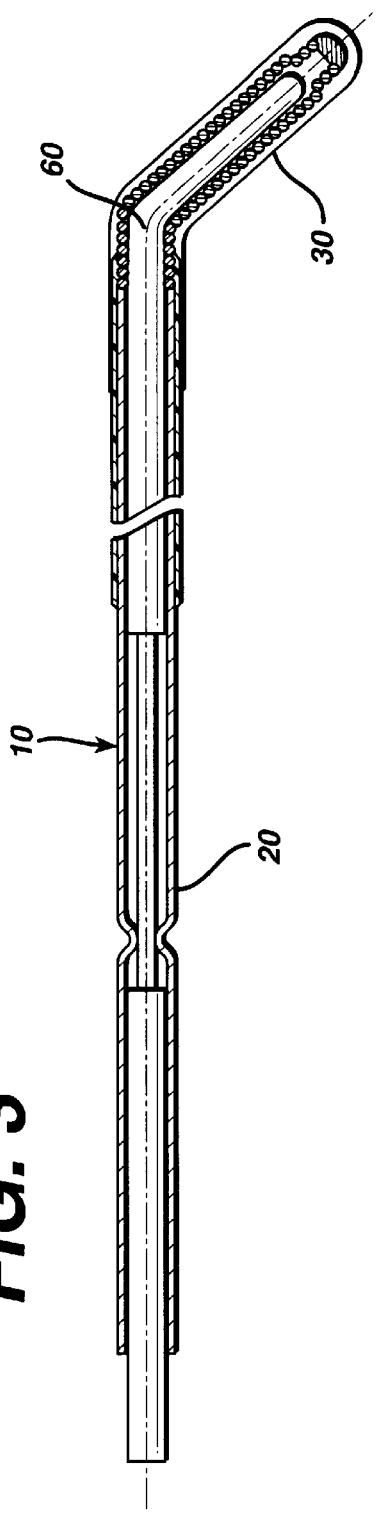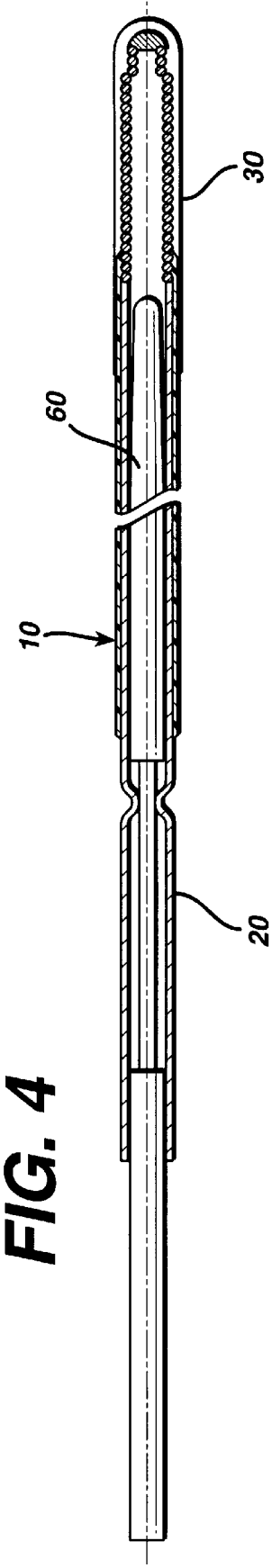

5,993,424

GUIDEWIRE HAVING A DISTAL TIP THAT CAN CHANGE ITS SHAPE WITHIN A VESSEL

This application is a continuation-in-part of U.S. application Ser. No. 08/693,378, filed Aug. 5, 1996, now abandoned.

FIELD OF THE INVENTION

The present invention relates to steerable guidewires for introducing medical catheters, such as balloon catheters, within the vasculature of patients. The present invention has even further relation to such a guidewire which can change the shape of its distal tip without being removed from the patient.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow. Typically, the balloon catheter is guided to the specific area within the vessel by an elongated guidewire. The guidewire is inserted into the patient and routed through the cardiovascular system and can be viewed on an x-ray imaging screen.

The path the guidewire follows during this procedure is often tortuous. The distal tip of the guidewire is flexible to avoid damaging inner walls of the blood vessels that the guidewire tip contacts along the tortuous path. The distal tip is often pre-bent to a desired configuration so that the guidewire can be inserted into branching blood vessels along its path. When the tip is pre-bent, the physician must be able to orient the tip so it can be pushed into these branching blood vessels. Examples of prior art guidewires are shown in U.S. Pat. No. 4,846,186 issued to Box et al. on Jul. 11, 1989 and U.S. Pat. No. 5,267,574 issued to Viera et al. on Dec. 7, 1993, both of which are hereby incorporated herein by reference.

Such guidewires typically have a core made from stainless steel or the like and coated with a lubricity enhancing agent, such as Teflon®. The distal end of the guidewire is not coated as such and usually comprises one or two tapered portions which reduce the diameter of the core wire at its distal end. The distal most portion of the core wire is then flattened to form a ribbon tip which makes it easier for a physician to form into a desired shape. A flexible coiled wire spring surrounds the distal tip of the core wire and is attached thereto. The coil separates from the core wire for a predetermined length and is attached proximal to the flattened distal portion of the core wire.

Other types of guidewires have cores which are made from superelastic alloys such as Nitinol®. An example of such a wire is given in U.S. Pat. No. 5,411,476 issued to Abrams et al. on May 2, 1995, which is hereby incorporated herein by reference. The superelastic nature of the core wire allows the metal to be deformed, as is typically the case as the guidewire travels through tortuous vessels, and restrained in the deformed condition, causing the alloy to transform from an austenite phase to a martensite phase. However, once the restraint on the superelastic member is removed, the stress is reduced and the core returns to its original undeformed shape by the transformation back to the original phase.

When the physician is navigating the tortuous paths of the human vasculature, it is often desirable to have the distal tip of the guidewire bent to a particular shape. This aids the guidewire in making turns into branching vessels or the like. However, during the same procedure, the physician may often want the distal tip of the guidewire to be flexible, not having a pre-bent configuration. This needs to be accomplished without removing the guidewire from the patient. Therefore, there has been a desire to have a guidewire whose tip shape can change without being removed from the body of a patient. The present invention fulfills such a desire.

SUMMARY OF THE INVENTION

In accordance with the present invention there is provided a guidewire for navigating through body vessels. The guidewire has a proximal end, a distal end and a longitudinal axis extending therebetween. The guidewire includes an outer tube having proximal and distal ends, wherein the distal end of the tube is a flexible distal tip having a smooth closed distal end. The guidewire further includes a core wire having distal and proximal ends. The core wire distal end is elastic and will return to a preformed shape upon the removal of any stress applied thereto. The core wire can slide longitudinally within the tube between a retracted position, where the core wire distal end is proximal to the flexible distal tip. In the retracted position the tube applies sufficient stress to deform the core wire distal end. The core wire also slides to an extended position, wherein said core wire distal end is within and substantially surrounded by the flexible distal tip. Placing the core wire in the extended position removes the stress so that said core wire distal end and the flexible distal tip assume the preformed shape.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

FIG. 3 is similar to that of FIG. 1 but showing the core wire in its extended position.

FIG. 4 is similar to that of FIG. 3 but showing the core wire in its retracted position.

DETAILED DESCRIPTION OF THE INVENTION

Figure 1:
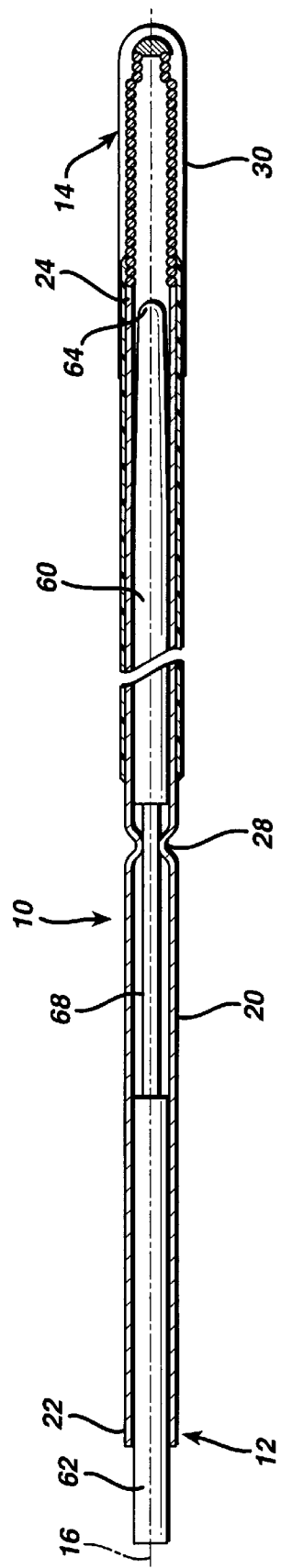
FIG. 1 is a simplified cross-sectional view of a guidewire made in accordance with the present invention.

Referring to the drawings wherein like numerals indicate the same elements throughout the views, there is shown in FIG. 1 a guidewire 10 made in accordance with the present invention. Guidewire 10 is a steerable percutaneous transluminal coronary angioplasty (PTCA) guidewire such as those described in U.S. Pat. No. 5,267,574 issued to Viera et al. on Dec. 7, 1993 or U.S. Pat. No. 4,846,186 issued to Box et al. on Jul. 11, 1989, both of which are hereby incorporated herein by reference. Guidewire 10 is designed to navigate through body vessels so as to guide and deliver balloon catheters and the like. Guidewire 10 has a proximal end 12, a distal end 14 and a longitudinal axis 16 extending therebetween. Guidewire 10 includes an outer tube 20. Tube 20 has a proximal end 22 and a distal end 24. As discussed below, outer tube 20 is preferably made from an elastic material and most preferably made from a superelastic material. Such materials are well known to those skilled in the art and include stainless steel, plastics, etc.

Figure 2:
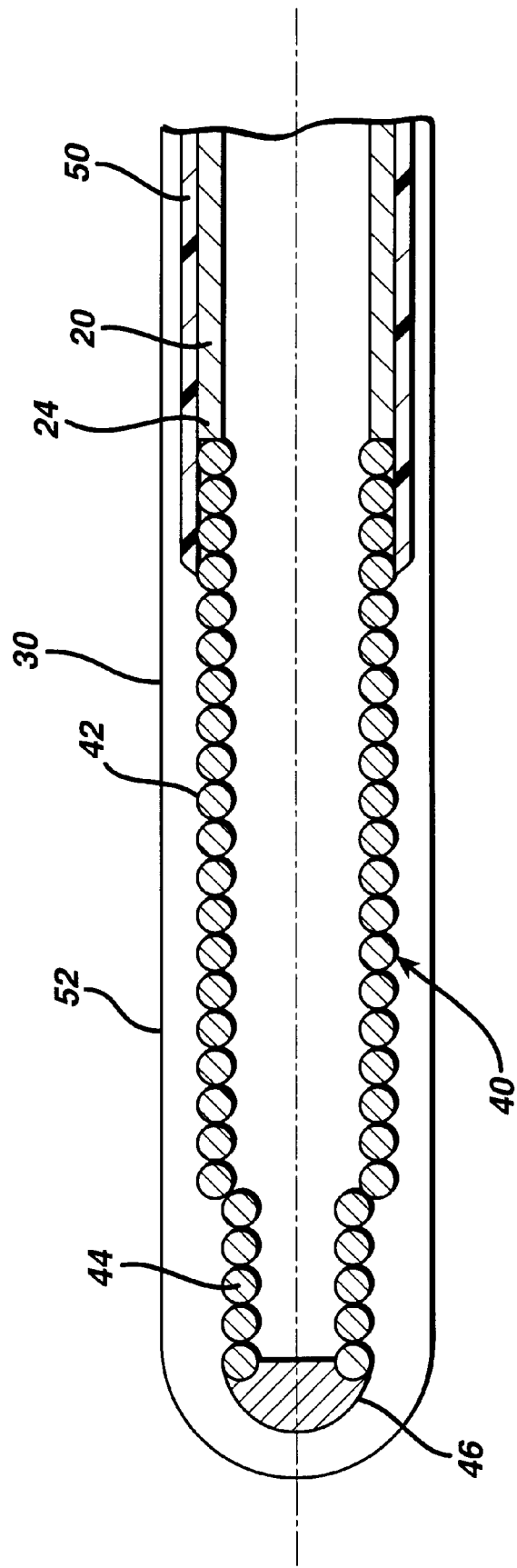
FIG. 2 is similar to that of FIG. 1 but showing the distal tip of the guidewire in greater detail.

Distal end 24 of tube 20 further includes a flexible distal tip 30, which can best be described by referring to FIG. 2. Distal tip 30 is attached to the outer tube 20. Flexible distal tip 30 is preferably includes a helical coil 40 and is attached to tube 20 by any means known to those skilled in the art including welding, soldering, adhesives, etc. Coil 40 is preferably made from an elastic material, and most preferably made from a superelastic material. This is so the coil will not permanently deform as it travels through the tortuous vasculalure. Use of such materials in medical devices is described in U.S. Pat. No. 5,067,957 issued to Jarvis on Nov. 26, 1991, which is hereby incorporated herein by reference. Coil 40 has a first uniform diameter region 42 and a second smaller uniform diameter region 44. This is so the tip 14 of the guidewire can accommodate a radiopaque marker band if desired. Coil 40 preferably includes a rounded tip weld 46 at the its proximal end thereby giving the tip a smooth closed distal end. This is to help prevent the tip from scraping against a vessel wall and damaging it. In addition, having a closed end prevents blood from entering the tube, which could alter performance of the guidewire. Coil 40 can also include radiopaque markers which are well known to those skilled in the art, or can be made from a radiopaque material.

Guidewire 10 includes a polytetrafluroethylene (PTFE) sleeve 50 which is heat shrunk over most of the length of tube 20 and extends distally to cover a portion of the coil 40. Sleeve 50 helps to connect coil 40 to tube 20. The distal end 30 is preferably coated with a hydrophilic coating 52 which adds lubricity to the guidewire and helps seal the distal end of the guidewire to prevent blood from entering the tube. Distal end 40 may include a polymer coating under the hydrophilic coating.

By referring back to FIG. 1, it can be shown that guidewire 10 further includes a core wire 60. Core wire 60 has distal end 64 and proximal end 62. The distal end of the core wire is manufactured so as to have a preformed shape, such as that shown in FIG. 3. Thereby, if any stress is applied to the distal end of the core wire so as to give it a shape other than its preformed shape, it will return to its preformed shape once the stress is removed.

Materials for the manufacture of the distal end of the core wire include Nitinol as was described in the hereinbefore incorporated Abrams reference. That is, superelastic distal end of lo the core wire, is preferably made of an alloy material consisting essentially of about 40 to about 49% titanium and the balance nickel and up to 10% of one or more other alloying elements. The other alloying elements may be selected from the group consisting of iron, cobalt, vanadium and copper. The alloy can contain up to about 10% copper and vanadium and up to 3% of the other alloying elements. The addition of nickel above the equiatomic amounts with titanium and the other identified alloying increase the stress levels at which the stress-induced Austenite-to-martensite transformation occurs and ensure that the temperature at which the martensite phase transforms to the austenite phase is well below human body temperature so that austenite is the only stable phase at body temperature. The excess nickel and additional alloying elements also help to provide an expanded strain range at very high stresses when the stress induced transformation of the austenite phase to the martensite phase occurs. The proximal end 62 need not be made from a super elastic material, which can reduce the cost. Core wire 60 is disposed within tube 20 such that it can slide longitudinally within said tube. Preferably the distal tip 64 of the core wire is tapered down to a smaller diameter.

The core wire slides between a retracted and extended position. In the retracted position, the distal end of the core wire is proximal to the flexible distal tip, as shown in FIGS. 1, 2 and 4. In the retracted position, the tube 20 applies sufficient stress to deform the core wire distal end distal end 64, and can substantially assume the shape of the outer tube 20. In the extended position, the distal end 64 of the core wire is distal to the distal end 24 of the outer tube and is substantially surrounded by the flexible distal tip, as shown in FIG. 3. In the extended position the stress is removed and core wire distal end 64, as well as the flexible distal tip, assumes the preformed shape. Preferably the core wire can also rotate within the tube 20 as well. The force required to bend tube 50 is greater than the force required to bend the distal end 64 of the core wire.

Guidewire 10 can then be guided through the vasculature of a patient through a combination of extending, retracting and rotating the core wire 60. Extending the core gives the distal tip 30 of the guidewire a bent shape to help it make turns within the vasculature. There are numerous pre-bent shapes known to those skilled in the art which could be imparted to the distal end 64 of core wire 60.

Guidewire 10 preferably includes a means for preventing the removal of the core wire from the outer tube 20. As seen from FIGS. 1, 3 and 4, outer tube 20 includes a flange 28 and core wire 60 has a reduced diameter area 68. Area 68 allows the core wire 60 to slide within the tube and flange 28 prevents the core wire from being retracted too far. In addition, it is preferable that the core wire always be proximal to the distal end 49 of the flexible distal tip when in the extended position. Flanges 28 as well as a closed distal end at the flexible distal tip such as provided by the coating 52 or bead 46, all act as a means for preverting the core wire distal end 64 from extending distal to distal end 14 of catheter 10.

Figure 5:
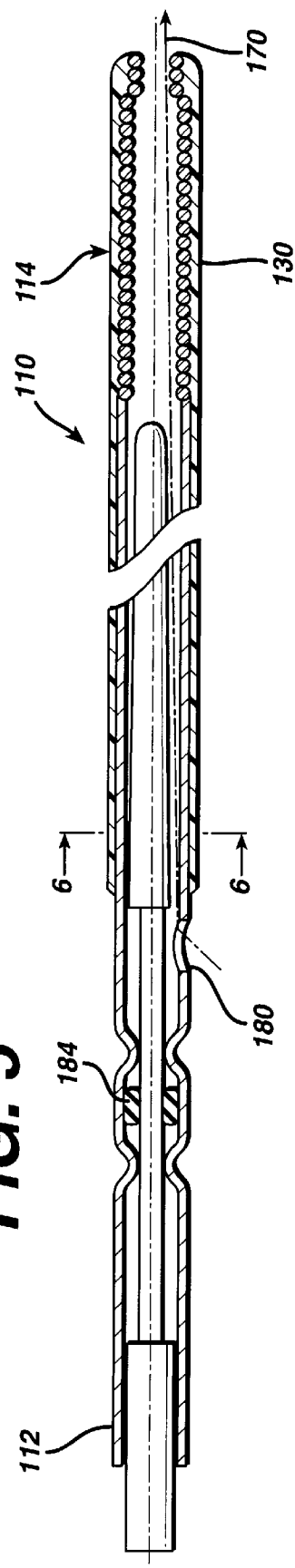
FIG. 5 is a view similar to that of FIG. 1 bit showing an alternative embodiment of a guidewire made in accordance with the present invention.
Figure 6:
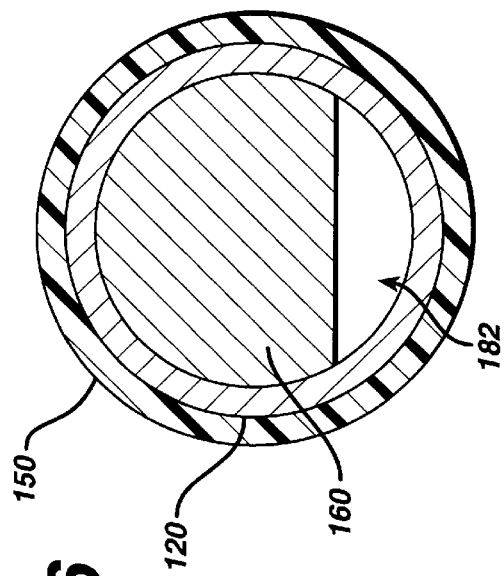
FIG. 6 is a cross-sectional view of the guidewire shown in FIG. 5 taken along line 6—6.

There is shown in FIG. 5 a guidewire 110 which is an alternative embodiment of a guidewire made in accordance with the present invention. Guidewire 110 is similar to guidewire 10 except that it includes an injection port 180 at proximal end 112. Injection port 180 allows fluids, such as contrast medium, to be injected through the guidewire and into the vasculature of a patient. The core wire proximal to the injection port must allow for the passage of fluid through the distal end 114 of catheter 110. As seen from FIG. 6, guidewire 110 preferably includes a heat shrunk PTFE sleeve 150 over outer tube 120. Core wire 160 has a semicircular cross section so as to create a channel or lumen 182 for passage of fluid therethrough. Guidewire 110 preferably includes a seal 184, made from any suitable material such as rubber, to prevent fluid from being delivered through the proximal end of the catheter. The distal tip 130 of catheter 110 would be open so as to allow for the passage of fluid in the direction of arrow 170.

Although particular embodiments of the present invention have been shown and described, modification may be made to the catheter without departing from the spirit and scope of the present invention. The terms used in describing the invention are used in their descriptive sense and not as terms of limitations.

What is claimed is:

1. A guidewire for navigating through body vessels, said guidewire having a proximal end, a distal end and a longitudinal axis extending therebetween, said guidewire comprising:
    a) an outer tube having proximal and distal ends, said distal end of said tube comprising a flexible distal tip;
    b) a core wire having distal and proximal ends, said core wire distal end being elastic and will return to a preformed shape upon the removal of any stress applied thereto, said core wire can slide longitudinally and rotate within said tube between a retracted position, where said core wire distal end is proximal to said flexible distal tip and said tube applies sufficient stress to deform said core wire distal end, and an extended position, wherein said core wire distal end is within and substantially surrounded by said flexible distal tip, thereby removing said stress so that said core wire distal end and said flexible distal tip assume said preformed shape; and
    c) a means for limiting the distance that said flexible distal tip of said core wire can be retracted into said tube.

2. The guidewire according to claim 1 wherein said flexible distal tip has a smooth closed distal end.

3. The guidewire according to claim 1 further including a means for preventing said distal end of said core wire from extending distal to said flexible distal tip.

4. The guidewire according to claim 1 wherein said distal tip of said core wire has a preformed shape which is at an angle to said longitudinal axis of said guidewire.

5. The guidewire according to claim 1 wherein said distal tip of said core wire comprises a superelastic alloy.

6. The guidewire of claim 5 wherein said superelastic alloy comprises of about 40 to about 49% titanium and the balance of the alloy being nickel and up to 10% of other alloying elements selected from the group consisting of iron, cobalt, vanadium and copper.

7. The guidewire according to claim 1 wherein said distal end of said guidewire tapers distally.

8. The guidewire according to claim 1 wherein said flexible distal tip of said guidewire comprises a coiled spring.

9. A guidewire for navigating through body vessels, said guidewire having a proximal end, a distal end and a longitudinal axis extending therebetween, said guidewire comprising:
    a) an outer tube having proximal and distal ends, said distal end of said outer tube comprising a flexible distal tip, said distal tip having an open distal end;
    b) a core wire having distal and proximal ends, said core wire distal end being elastic and will return to a preformed shape upon the removal of any stress applied thereto, said core wire can slide longitudinally and rotate within said tube between a retracted position, where said core wire distal end is proximal to said flexible distal tip and said tube applies sufficient stress to deform said core wire distal end, and an extended position, wherein said core wire distal end is within and substantially surrounded by said flexible distal tip, thereby removing said stress so that said core wire distal end and said flexible distal tip assume said preformed shape, said core wire distal end being proximal to said flexible tip distal end in its extended position;
    d) a fluid port on said proximal end of said guidewire, and a channel within said guidewire providing fluid communication between said fluid port and said distal end of said flexible distal tip;
    e) a means for limiting the distance that said flexible distal tip of said core wire can be retracted into said tube.

10. The guidewire according to claim 9 further including a means for preventing said distal end of said core wire from extending distal to said flexible distal tip.

11. The guidewire according to claim 9 wherein said distal tip of said core wire has a preformed shape which is at an angle to said longitudinal axis of said guidewire.

12. The guidewire according to claim 9 wherein said distal tip of said core wire comprises a superelastic alloy.

13. The guidewire of claim 12 wherein said superelastic alloy comprises of about 40 to about 49% titanium and the balance of the alloy being nickel and up to 10% of other alloying elements selected from the group consisting of iron, cobalt, vanadium and copper.

14. The guidewire according to claim 9 wherein said distal end of said guidewire tapers distally.

15. The guidewire according to claim 9 wherein said flexible distal tip of said guidewire comprises a coiled spring.

16. The guidewire according to claim 9 further including a seal, proximal to said fluid port so as to prevent fluid communication between said fluid port and said proximal end of said guidewire.

17. A guidewire for navigating through body vessels, said guidewire having a proximal end, a distal end and a longitudinal axis extending therebetween, said guidewire comprising:
    a) an outer tube having proximal and distal ends, said distal end of said outer tube comprising a flexible distal tip attached to said distal end of said outer tube and extending distally thereto, said distal tip comprising a coiled spring;
    b) a core wire having distal and proximal ends, said core wire distal end being elastic and will return to a preformed shape upon the removal of any stress applied thereto, said core wire can slide longitudinally and rotate within said tube between a retracted position, where said core wire distal end is proximal to said flexible distal tip and said tube applies sufficient stress to deform said core wire distal end, and an extended position, wherein said core wire distal end is within and substantially surrounded by said flexible distal tip, thereby removing said stress so that said core wire distal end and said flexible distal tip assume said preformed shape, said core wire distal end being proximal to said flexible tip distal end in its extended position; and
    c) means for preventing said distal end of said core wire from extending distal to said flexible distal tip, and a means for limiting the distance that said flexible distal tip of said core wire can be retracted into said tube.

18. The guidewire according to claim 17 wherein said distal tip of said core wire has a preformed shape which is at an angle to said longitudinal axis of said guidewire.

19. The guidewire according to claim 17 wherein said distal tip of said guidewire tapers distally.

20. The guidewire according to claim 17 wherein said core wire distal end is made from a superelastic alloy.

21. The guidewire of claim 20 wherein said superelastic alloy comprises of about 40 to about 49% titanium and the balance of the alloy being nickel and up to 10% of other alloying elements selected from the group consisting of iron, cobalt, vanadium and copper.

* * * * *